US010602740B2

(12) United States Patent
Kravitz et al.

(10) Patent No.: US 10,602,740 B2
(45) Date of Patent: Mar. 31, 2020

(54) ORGAN PERFUSION APPARATUS WITH DOWNSTREAM FLOW CONTROL

(75) Inventors: David Kravitz, Barrington Hills, IL (US); Christopher P. Steinman, Sandy, UT (US); Jeffrey S. Louis, Akron, OH (US); Matthew Copithorne, Farmingham, MA (US); Brian L. Otts, Warrior, AL (US); Peter Demuylder, Steenhuffel (BE)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 365 days.

(21) Appl. No.: 13/545,281

(22) Filed: Jul. 10, 2012

(65) Prior Publication Data

US 2014/0017662 A1    Jan. 16, 2014

(51) Int. Cl.
    *A01N 1/02*     (2006.01)
(52) U.S. Cl.
    CPC ................... *A01N 1/0247* (2013.01)
(58) Field of Classification Search
    CPC .................................................. A01N 1/0247
    USPC ............................................................ 435/1.2
    See application file for complete search history.

(56) References Cited

U.S. PATENT DOCUMENTS

| | | | |
|---|---|---|---|
| 4,745,759 A | 5/1988 | Bauer et al. | |
| 5,188,604 A | 2/1993 | Orth | |
| 5,338,662 A | 8/1994 | Sadri | |
| 5,368,555 A | 11/1994 | Sussman et al. | |
| 7,410,474 B1 | 8/2008 | Friend et al. | |
| 7,476,200 B2 | 1/2009 | Tal | |
| 7,824,848 B2 | 11/2010 | Owen et al. | |
| 8,109,906 B2 | 2/2012 | Smisson, III et al. | |
| 2004/0191116 A1 | 9/2004 | Jarvik et al. | |
| 2005/0147958 A1 | 7/2005 | Hassanein et al. | |
| 2005/0255442 A1 | 11/2005 | Brassil et al. | |
| 2006/0148062 A1 | 7/2006 | Hassanein et al. | |
| 2007/0009881 A1 | 1/2007 | Arzt et al. | |
| 2008/0286746 A1 | 11/2008 | Poo et al. | |
| 2010/0028850 A1 | 2/2010 | Brassil | |
| 2010/0092939 A1 | 4/2010 | Belous et al. | |
| 2011/0054283 A1* | 3/2011 | Shuler ............... | A61B 5/14539 600/364 |
| 2011/0076666 A1 | 3/2011 | Brassil | |
| 2011/0136096 A1 | 6/2011 | Hassanein et al. | |
| 2011/0236875 A1 | 9/2011 | Lee et al. | |
| 2011/0300615 A1 | 12/2011 | Owen et al. | |

FOREIGN PATENT DOCUMENTS

| | | |
|---|---|---|
| EP | 2301337 A2 | 3/2011 |
| EP | 2 775 828 B1 | 5/2018 |
| WO | 94/06292 A1 | 3/1994 |
| WO | WO 94/06292 A1 | 3/1994 |
| WO | 96/29865 A1 | 10/1996 |
| WO | WO 99/15011 | 4/1999 |
| WO | WO 00/60936 A1 | 10/2000 |
| WO | WO 2009/138446 A2 | 11/2009 |
| WO | WO 2013/068751 A2 | 5/2013 |

OTHER PUBLICATIONS

Shigeta et al., "A Basic Consideration for Porcine Liver Preservation Using a Novel Continuous Machine Perfusion Device," *Transplantation Proceedings*, 2012, vol. 44, pp. 942-945.
Shigeta et al., "Functional Recovery of Donation After Cardiac Death Liver Graft by Continuous Machine Perfusion Preservation in Pigs," *Transplantation Proceedings*, 2012, vol. 44, pp. 946-947.
Guarrera et al., "Hypothermic Machine Perfusion of Liver Grafts for Transplantation: Technical Development in Human Discard and Miniature Swine Models," *Transplantation Proceedings*, 2005, vol. 37, pp. 323-325.
Guarrera et al., "Hypothermic Machine Preservation in Human Liver Transplantation: The First Clinical Series," *American Journal of Transplantation*, 2009, vol. 9, pp. 1-10.
Van Der Plaats et al., "The Groningen Hypothermic Liver Perfusion Pump: Functional Evaluation of a New Machine Perfusion System," *Annals of Biomedical Engineering*, Oct. 26, 2006, vol. 34, No. 12, pp. 1924-1934.
Monbaliu Diethard et al., "Flow competition between hepatic arterial and portal venous flow during hypothermic machine perfusion preservation of porcine livers," *The International Journal of Artificial Organs*, Feb. 1, 2012, vol. 35, No. 2, pp. 119-131.
Feb. 7, 2014 International Search Report issued in International Patent Application No. PCT/US2013/049573.
Feb. 7, 2014 Written Opinion issued in International Patent Application No. PCT/US2013/049573.
Apr. 24, 2014 International Search Report issued in International Patent Application No. PCT/US2013/049573.
Apr. 24, 2014 Written Opinion issued in International Patent Application No. PCT/US2013/049573.
Nov. 14, 2014 Written Opinion and International Preliminary Report issued in PCT/US2013/049573.
Jan. 13, 2015 International Preliminary Report on Patentability issued in PCT/US2013/049573.
Mar. 7, 2017 Office Action issued in Japanese Application No. 2015-521688.
Mar. 21, 2017 Office Action issued in Chinese Application No. 201380046850.9.
Jun. 21, 2016 Office Action issued in Chinese Application No. 201380046850.9.

(Continued)

*Primary Examiner* — Susan M Hanley
(74) *Attorney, Agent, or Firm* — Oliff PLC

(57) ABSTRACT

An organ perfusion apparatus may include at least two tubes connected to an organ or tissue. A method of perfusing an organ or tissue may include connecting a first end of each of the at least two tubes to an organ or tissue, applying a fluid motive force to a perfusion fluid in the two tubes to force the fluid through the two tubes into the organ or tissue, and perfusing the organ or tissue through the at least two tubes such that the fluid motive force, provided by, e.g., a pump, and backpressure generated by the organ or tissue, establishes a flow balance between the at least two tubes. The flow balance may be altered without altering the fluid motive force that is applied.

6 Claims, 3 Drawing Sheets

(56) References Cited

OTHER PUBLICATIONS

Jan. 22, 2019 Office Action issued in Japanese Patent Application No. 2015-521688.
Jun. 18, 2019 Office Action issued in European Patent Application No. 13 740 121.2.
Jun. 11, 2019 European Search Report issued in European Patent Application No. 19 16 0037.
Jun. 11, 2019 Written Opinion issued in European Patent Application No. 19 160 037.8.
Jun. 11, 2019 European Search Report issued in European Patent Application No. 19 16 0027.
Jun. 11, 2019 Written Opinion issued in European Patent Application No. 19 160 027.9.
Van Der Plaats, A., "The Groningen Hypothermic Liver Perfusion Pump: Functional Evaluation of a New Machine Perfusion System", Annals of Biomedical Engineering, vol. 34, No. 12, pp. 1924-1934, 2006.
Jun. 28, 2018 Office Action issued in European Patent Application No. 13 740 121.2.
Mar. 6, 2018 Office Action issued in Japanese Application No. 2015-521688.
May 2, 2019 Office Action issued in Canadian Patent Application No. 2,917,823.

* cited by examiner

ORGAN PERFUSION APPARATUS WITH DOWNSTREAM FLOW CONTROL

BACKGROUND

Related technical fields include organ perfusion apparatuses capable of monitoring, sustaining and/or restoring the viability of the organ(s) and for storing and/or transporting the organ(s).

Various perfusion devices have been developed for storing and/or transporting an organ. For example, U.S. Pat. No. 7,824,848 discloses an example of an organ perfusion apparatus capable of perfusing an organ at hypothermic and/or normothermic temperatures.

SUMMARY

Perfusion apparatuses may be used for storage, transportation, diagnosis and/or treatment of harvested or engineered organs or tissue, and their main purpose is to maintain the organ or tissue in a viable state. However, more flexibility is desirable to allow clinicians to change specific parameters in the perfusion apparatus, e.g., the flow rate of the perfusate through the organ or tissue. Flow rates may preferably be adjusted based on research models and various clinical protocol(s) to ensure best possible outcomes of the perfused organ or tissue. For ease of reference herein, the term "organ" will mean organ and/or tissue unless otherwise indicated.

Embodiments include a method of perfusing an organ wherein a flow balance of perfusate flowing into an organ in a plurality of tubes connected to the organ is altered, for example, by a clinician using, for example, one or more valve. After altering the flow balance between the plurality of tubes connected to the organ, the clinician has the ability to measure an effect on the organ resulting from altering the flow balance. Also, the clinician preferably has the ability to measure or monitor the flow rate of the fluid in the plurality of tubes using, for example, one or more sensor.

DETAILED DESCRIPTION OF EMBODIMENTS

Figure 1:
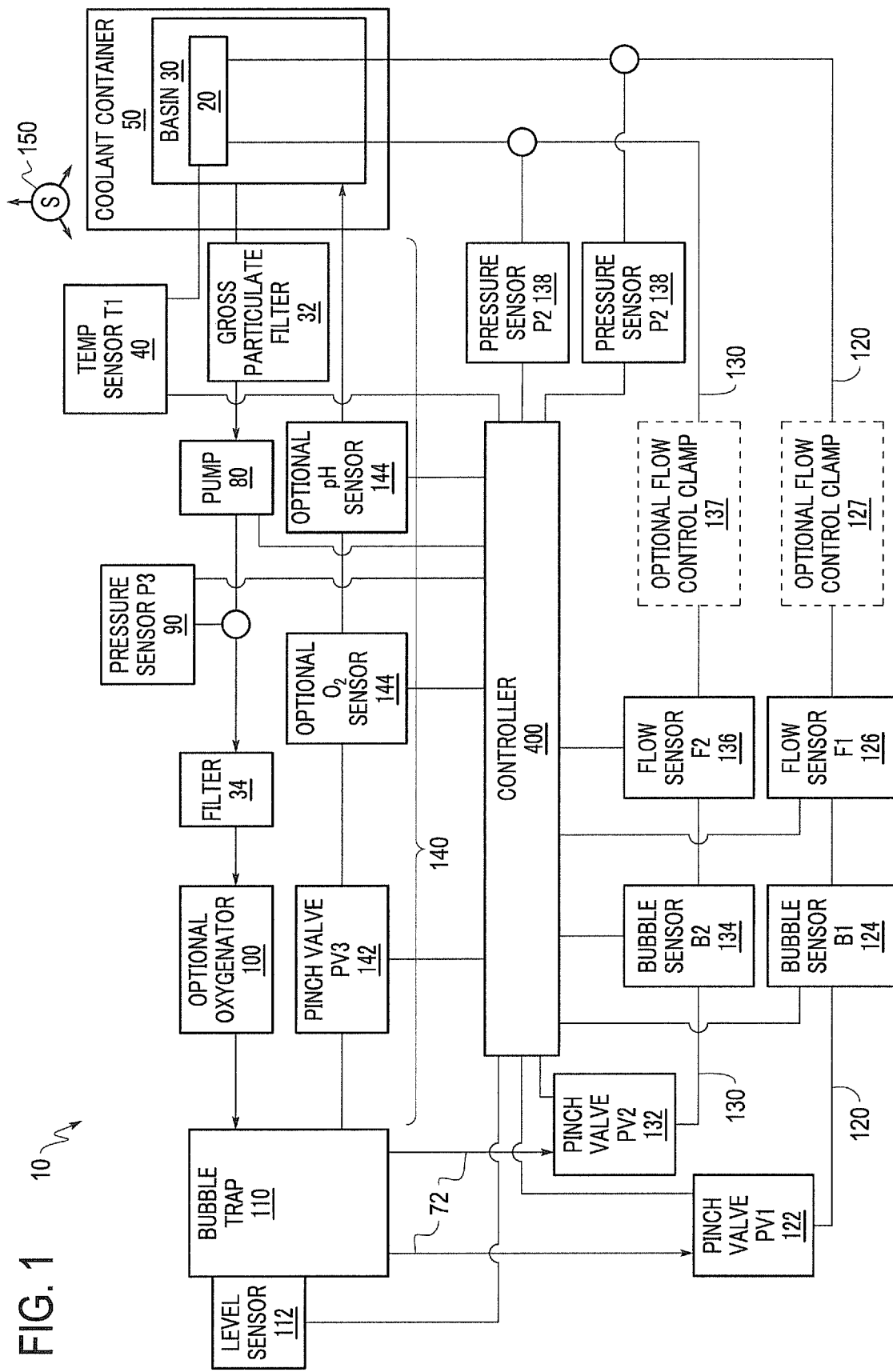
FIG. 1 is a schematic diagram of an exemplary organ perfusion apparatus according to the invention.

The following exemplary implementations refer to a perfusion apparatus, transport apparatus, and/or storage apparatus for an organ. It should be appreciated that, although the exemplary systems and methods according to this disclosure may be applicable to specific applications, the depictions and/or descriptions included in this disclosure are not intended to be limited to any specific application. Any perfusion apparatus for an organ that is to be perfused through two or more routes as described in an exemplary manner in this disclosure is contemplated.

According to exemplary implementations, an organ is connected to a plurality of tubes for perfusing fluid through the organ. The organ will innately provide backpressure on the fluid if the flow rate of the fluid is above a minimal threshold. A method of perfusing an organ includes connecting a first end of each of a plurality of tubes (e.g., two or more tubes) to an organ, for example via respective cannulae, and applying a fluid motive force to the fluid in the plurality of tubes to force the fluid through the plurality of tubes into the organ. A fluid motive force is a force that causes fluid to flow, e.g., a pressure differential caused by a pump, a height difference, or any other suitable structure and/or configuration. A flow balance between the plurality of tubes may be established by the fluid motive force and the innate backpressure provided by the organ. After the flow balance is established, for example, under normal perfusion conditions for the type of organ involved, the flow balance between the plurality of tubes may be altered without altering the fluid motive force that is applied and without altering the organ.

In exemplary implementations, the first end of each of the plurality of tubes may be connected to different vasculature of the organ. For example, the first end of each of two tubes may be connected to one of two vasculature systems of the organ (e.g., one to the hepatic artery and one to the portal vein of a liver).

In exemplary implementations, the fluid motive force is a force necessary to drive fluid through the plurality of tubes into the organ. The fluid motive force may be applied by a pump. The pump may be a roller pump, a centrifugal pump, a peristaltic pump or any pump that provides suitable pumping characteristics. The pump may be preferably disposed such that it does not come into contact with the perfused fluid. The fluid motive force may be applied by pumping fluid in, for example, a non-pulsatile manner. Alternatively, the fluid may be pumped in a pulsatile manner. Also, the fluid may be pumped in any combination of non-pulsatile and pulsatile manners. The fluid motive force may be applied by other means, for example, a gravity feed.

In exemplary implementations, the flow balance between the plurality of tubes may be altered, for example, by constricting at least one of the plurality of tubes to restrict fluid flow. For example, at least one valve may be disposed on at least one of the plurality of tubes. The at least one valve can be operated to constrict the tube on which it is disposed to restrict fluid flow, and thereby alter the flow balance among the tubes. Alternatively, valves that allow fluid to flow through the valve itself to control flow, instead of constricting a tube, may be used. The at least one valve may be manually controlled and/or electronically controlled. The configuration may include a plurality of valves, wherein at least one valve may be disposed on each of the plurality of tubes, capable of restricting fluid flow in its respective tube.

In exemplary implementations, a new flow balance may be established after altering the flow balance between the plurality of tubes. The previous flow balance (e.g., a flow balance before alteration) may be the flow balance between the plurality of tubes under normal operating conditions for the specific organ or for a given type and/or size of organ, or alternatively, may be a flow balance established by a previous alteration of the flow balance between the plurality of tubes. The previous flow balance may be a manually controlled flow balance between the plurality of tubes. The new flow balance may be established after a period of delay after altering the original flow balance, which may occur because of non-instantaneous reaction of the organ to the altered flow. The manually controlled flow balance may work in concert with, for example, firmware in a suitable controller, which may allow the clinician to vary the flow rate and/or pressure. The method of perfusing an organ may include measuring a period of time over which the new flow balance is established. For example, after the previous flow balance is altered, the perfusion apparatus and organ may require a certain amount of time before a new flow balance is established. Thus, it may be advantageous to determine the amount of time it takes for the perfusion apparatus to establish a new flow balance, e.g., in order to control sensors to determine the changes in flow rate and/or pressure of the fluid in the tubes and/or to determine any need for further adjustment of one or more valve. The apparatus' firmware may, for example, control and ramp up the flow rate and/or pressure over a period of time to avoid exceeding limits (e.g., preset flow rate and/or pressure limits).

Exemplary implementations may include measuring an effect on the organ resulting from altering the flow balance between the plurality of tubes. For example, a clinician may perform histological, pathological and/or enzymatic testing on the organ, and investigate how the organ reacts to the changed conditions. Exemplary implementations may include measuring a flow rate and/or pressure of the fluid in each of the plurality of tubes after altering the flow balance. This may allow the clinician to determine the changes in the flow rate and/or pressure of the fluid in real-time after altering the flow balance, allowing the clinician more control and precision in changing and documenting perfusion apparatus parameters and organ reactions. For example, at least one sensor may be disposed on or near at least one of the plurality of tubes and configured to measure the flow rate and/or pressure of fluid in the tube. The sensor may optionally be a non-contact sensor such as an ultrasonic flow sensor. The sensor may be controlled to continuously operate during perfusion. Alternatively, the sensor may be controlled to periodically operate during perfusion. The sensor may be disposed in close proximity to the organ, for example, about 2 inches to 3 inches or more from the organ. The upstream portion of the plurality of tubes between the sensor and the organ may be a straight length portion or a non-straight length portion. A plurality of sensors may be included. If a plurality of sensors is included, optionally, at least one sensor is disposed on or near each of the plurality of tubes and configured to measure the flow rate and/or pressure of the fluid in the tube.

Figure 3:
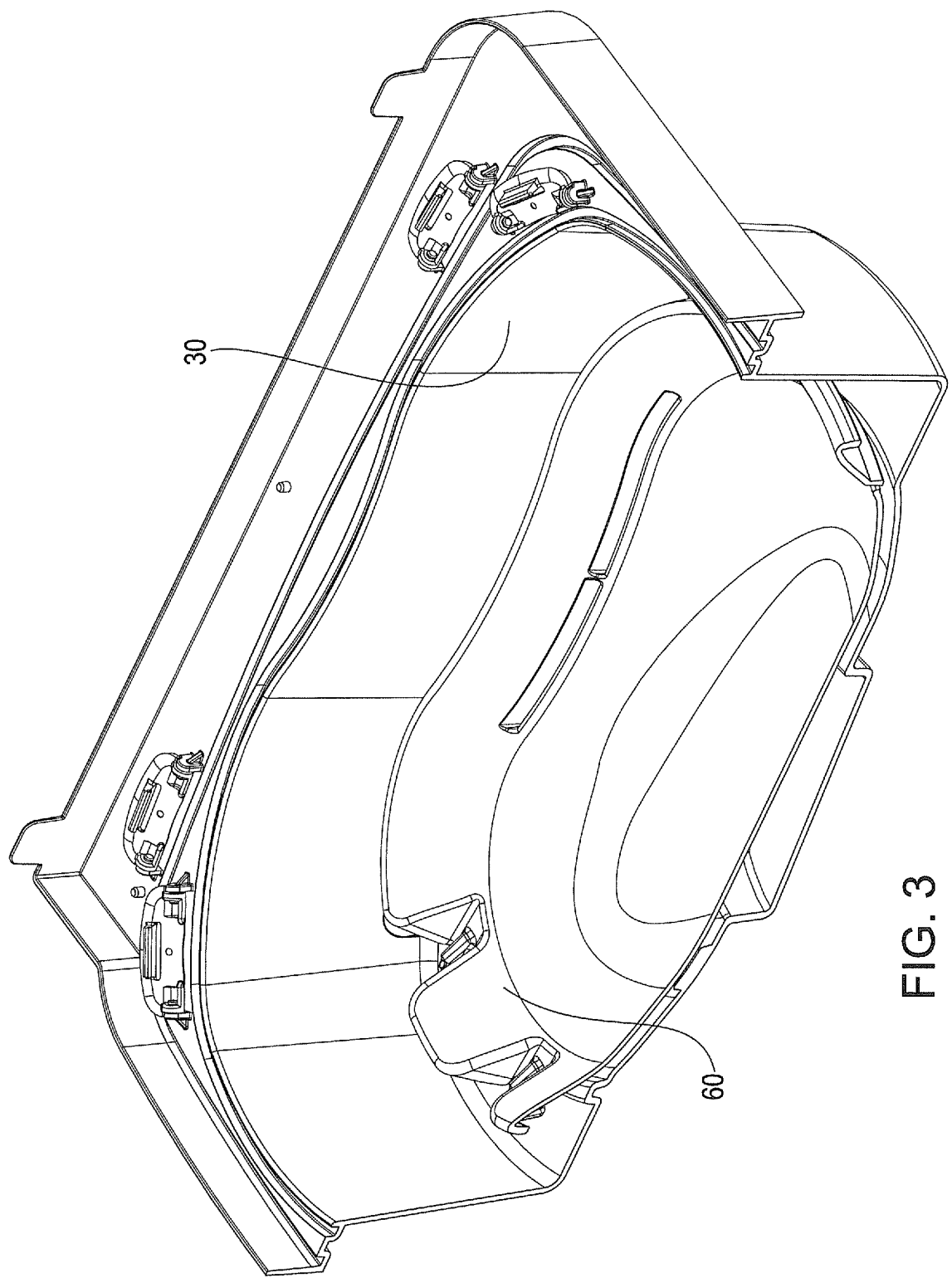
FIG. 3 is a cross-section of a perspective view of an exemplary cradle and basin of an organ perfusion apparatus.

FIG. 1 is a schematic diagram of a perfusion apparatus, such as a transport and/or storage apparatus 10, for an organ 20. The organ 20 may optionally be a liver but may be any human or animal, natural or engineered, healthy, injured or diseased organ or tissue that may be perfused through two or more perfusate entry paths. The depicted apparatus includes a basin 30 in which the organ may be placed. The basin 30 may hold a cradle 60 (as shown in FIG. 3), which preferably includes a surface on which the organ 20 is preferably disposed when the organ 20 is in the apparatus 10. The basin 30 may include a first filter that can function as a gross particulate filter. The basin 30 and/or the cradle 60 are preferably configured to allow a perfusate bath to form around the organ 20. The apparatus 10 or basin 30 may also include a temperature sensor 40 located in or near the cradle 60. Multiple temperature sensors 40 may provide redundancy in the event of a failure and/or may provide temperature measurement at multiple locations. Preferably, the temperature sensor 40 is an infrared temperature sensor. The temperature sensor 40 is preferably disposed as close as practical to the organ 20 when the organ 20 is disposed in the cradle 60 in order to improve the usefulness and accuracy of the temperature sensors 40, which preferably provide a temperature measurement of the perfusate that may be correlated to a temperature of the organ 20. Alternatively or additionally, the temperature sensor 40 may be used to directly measure the temperature of the organ 20.

The basin 30 is preferably disposed within a coolant container 50 that may contain cold materials such as ice, ice water, brine or the like. Coolant container 50 may be permanently or removably attached to, or an integral, monolithic part of, apparatus 10. Thus, in use, the organ 20 is disposed within the cradle 60 and/or the basin 30, which is disposed within the coolant container 50. Preferably, each of the basin 30, cradle 60 and coolant container 50 is configured, or keyed, to fit within its corresponding mating component in a single orientation. The configuration of the coolant container 50, basin 30 and cradle 60 may provide a configuration that provides cooling for the organ 20 without the contents of coolant container 50 contacting the organ 20 or the cradle 60. Although the coolant container 50 is described herein as containing ice, any suitable cooling medium can be used. Ice may be preferable due to the ease with which ice can be procured, but one of ordinary skill would understand that any suitable cooling medium, which could be an active cooling medium (such as a thermo electric cooler or a refrigerant loop) or a passive cooling medium similar to ice or ice water, or a combination thereof, may be utilized. The amount of ice, or other cooling medium, that can be placed within the coolant container 50 should be determined based upon the maximum time that cooling is to be provided while the organ 20 will be in the apparatus 10.

The cradle 60 may include components configured to securely restrain the organ 20 in place. Such components may, for example, include user selectable netting that is fastened to the cradle 60.

After passing through the filter, the perfusate flows along a first flow path 70 that includes a suitable fluid conduit 72, such as flexible or rigid tubing, a pump 80, a pressure sensor 90, a second filter, an optional oxygenator 100 and a bubble trap 110, each of which is discussed below.

The first filter is preferably a relatively coarse filter (relative to the second filter). Such a coarse filter may be provided to prevent large particles, which may for example be byproducts of the organ or of the organ being removed from the donor, from entering and clogging fluid paths of the apparatus 10. The first filter may be an integral part of the basin 30 or the first filter may be disposed elsewhere in the first flow path 70 downstream of the basin 30. The first filter may also be a separate component from the basin 30 or disposed within the fluid conduit 72.

The first flow path 70 may also include a pump 80, or another pressure head such as a gravity head. The pump 80 may be any pump that is suitable in connection with perfusing of organs. The pump 18 may include a single pump or multiple pumps. Examples of suitable pumps may include hand operated or motor-operated pumps, such as centrifugal pumps or roller pumps. If a roller pump is included, the roller pump may include a single channel or flow path (where only one tube is compressed by the rollers) or the roller pump may include multiple, parallel channels or flow paths (where multiple tubes are compressed by the rollers). If multiple, parallel channels or flow paths are included, the rollers may preferably be disposed out of phase or offset so that pulses created by the rollers are out of phase, which may result in a fluid flow out of the roller pump that is relatively less pulsatile than would be the case with a single roller. Such a multiple channel roller pump may achieve a constant flow rate or a minimally pulsatile flow rate, which may be advantageous depending on the other components in the flow path and/or the type of organ being perfused.

In a method of perfusing the organ 20, the pump may be used to apply a fluid motive force to perfusion fluid in conduit 72. The pump 80 may pump the perfusate through the fluid conduit 72 into the organ 20. The fluid motive force should be adequate to pump fluid through the fluid conduit 72 into the organ 20. For example, the fluid motive force may result in flow rates between 0.3 L/min and 2.0 L/min, adjustable in 0.1 L/min increments. For example, a portal vein vasculature pressure may be between 5 mm/Hg and 20 mm/Hg, e.g., about 10 mm/Hg. For example, a hepatic artery vasculature may be between 20 mm/Hg and 40 mm/Hg, e.g., about 30 mm/Hg. As discussed above, the pump 80 may generate a pulsatile or non-pulsatile flow, or a combination of pulsatile and non-pulsatile flow.

The fluid conduit 72 may include a plurality of tubes. For example, the plurality of tubes may include one or more tubes that extend from the basin 30 to the bubble trap 110, one or more tubes that extend downstream from the bubble trap 110, and two or more tubes that extend to the organ 20, such as one tube that may extend along the portal flow path 120 and be connected to the portal vein of a liver, and another tube that may extend along the hepatic flow path 130 and be connected to the hepatic artery of the liver. The fluid motive force from the pump 80 and the backpressure provided by the organ 20 establish a flow balance between the plurality of tubes.

The flow path 70 may include a pressure sensor 90. The pressure sensor 90 may preferably be disposed after the outlet of the pump 80 in order to monitor and/or be used to control the pressure produced at the outlet of the pump by way of a suitable controller 400, which may include a processor and other suitable electronics to operate software. For example, the controller 400 may control the pressure sensor 90 to periodically or continuously monitor the pressure of the fluid flowing out of the pump 80. If the controller 400 receives a signal from the pressure sensor 90 that the pressure of the fluid is outside of a predetermined range, the controller may control the pump 80 to stop pumping fluid, and may also shut down some or all other active features of the perfusion apparatus and/or provide a warning signal to the clinician.

The flow path 70 may include an oxygenator 100 such as an oxygenator membrane or body to provide oxygenation to the perfusate. Oxygen may be provided to the oxygenator 100 by any suitable means. Suitable oxygen sources may include pure oxygen or mixed gases such as air. The gas may be compressed, such as in a high-pressure cylinder, liquefied as would be stored in a dewar, or drawn from the surrounding atmosphere. Preferably, the oxygen may be provided by way of an oxygen generator, which may be separate from the apparatus 10 or integral to the apparatus 10. Oxygen may be generated through any suitable means, some examples of which include through pressure swing adsorption using a molecular sieve, through a ceramic oxygen generator (a solid state oxygen pump), or through decomposition of water.

The flow path 70 may include a bubble trap 110. The bubble trap 110 preferably separates gas bubbles that may be entrained in the perfusate flow and prevents such bubbles from continuing downstream and entering the organ 20. The bubble trap 110 may also function as an accumulator that reduces or eliminates pulsatility of the perfusate flow. The bubble trap 110 may include a volume of gas, initially or through the accumulation of bubbles, such that pressure fluctuations in the perfusate are dampened or eliminated.

The bubble trap 110 may include a vent that allows purging of gas during start up or a purging process. The vent may be connected to or part of purge flow path 140 (which is discussed in more detail below). The vent is preferably open during a start up process so that any air or other gas may be purged from the perfusate path 70. Once the gas is purged from the perfusate path 70, the vent may preferably be closed. The vent may be closed manually or may be closed automatically by way of the controller 400.

The bubble trap 110 may include a level sensor 112. A level sensor 112 may optionally be used during the purging process to determine when the purging is complete and/or may be used to determine when the purging process needs to be repeated, which may happen after bubbles have been trapped in the bubble trap 110. Also, through the use of the level sensor 112 and the vent, the accumulator function of the bubble trap can be tuned to account for differing amplitudes and frequencies of pulsatility in the perfusate flow.

The bubble trap 110 may have any number of outlets, as needed or desired for a given application of the perfusion apparatus. In FIG. 1, three outlets are shown connected to three different flow paths, which may be particularly suited for the perfusion of a liver. When perfusing a liver, the three paths preferably include portal flow path 120 connected to the portal vein of a liver, hepatic flow path 130 connected to the hepatic artery of a liver, and bypass flow path 140 that provides a return path to the basin 30. The various paths may extend directly from the bubble trap 110 or from a manifold or jointed tubing downstream of the bubble trap 110.

As shown in FIG. 1, the portal flow path 120 and hepatic flow path 130 may optionally include similar or different components such as valves 122, 132; bubble sensors 124, 134; flow sensors 126, 136; flow control clamps 127, 137; and pressure sensors 128, 138. Each similar component may function in a similar manner, and such pairs of components may optionally be structurally and/or functionally identical to reduce manufacturing costs.

Valves 122, 132 may be pinch valves that function to squeeze tubing and reduce or shut off flow, but any suitable valve may be used. Pinch valves may be advantageous because in normal usage they do not come into contact with the perfusate and therefore do not require replacement and/or cleaning after use.

Optionally, the bubble sensors 124, 134 are non-contact—e.g., ultrasonic—sensors disposed around tubing, although any suitable sensor may be used. Similar to pinch valves, ultrasonic sensors may be advantageous because in normal usage they do not come into contact with the perfusate and therefore do not require replacement and/or cleaning after use. Instead, ultrasonic sensors can be disposed in contact with, adjacent to or around an external surface of tubing in order to sense bubbles.

Optional pressure sensors 128, 138 may constitute a set of sensors in the apparatus 10 that continuously or periodically detect the pressure of the perfusate flowing in the tubes that extend to the organ 20, such as the portal flow path 120 and the hepatic flow path 130. The pressure sensors 128, 138 may be disposed in or near the perfusate path, and any suitable pressure sensor contemplated by a person of ordinary skill in the art may be used. The pressure sensors 128, 138 may be disposed in close proximity to the organ 20. For example, the pressure sensors 128, 138 may be located in the tubes upstream of, or even in, cannulae attached to vasculature of the organ 20. The pressure sensors 128, 138 may be located downstream of the flow control clamps 127, 137. The pressure sensors 128, 138 may be located on, for example, a printed circuit board positioned in the apparatus 10 (e.g., positioned in a flat, flange portion of the basin 30). Pressure sensors 128, 138 close to the organ 20 may provide more accurate measurements of the pressure in the portal flow path 120 and the hepatic flow path 130 than pressure sensors 128, 138 further away from the organ. Increasing the size of the tubing may allow the pressure sensors 128, 138 to be located further away from the organ 10 while still providing sufficient accuracy. If the pressure sensors 128, 138 are in fluid communication with the perfusate, they are preferably disposable and easily removable from the apparatus 10.

Optional flow sensors 126, 136 constitute a set of sensors in the apparatus 10 that periodically or continuously detect the flow rate of the perfusate flowing in the tubes that extend to the organ 20, such as the portal flow path 120 and the hepatic flow path 130. For example, one of the two flow sensors 126, 136 is disposed on each of the two tubes, each of the flow sensors 126, 136 configured to measure the flow rate of fluid in each of the two tubes. The flow sensors 126, 136 may be configured to measure real-time flow rate of the perfusate. The flow sensors 126, 136 may be ultrasonic transit-time sensors, but any suitable sensors contemplated by a person of ordinary skill in the art may be used. As discussed above, ultrasonic sensors may be advantageous because they are not in fluid communication with the perfusate and thus may be reusable. The flow sensors 126, 136 are preferably disposed in close proximity to the organ in order to more accurately determine the flow rate of the perfusate, but are preferably disposed upstream of the pressure sensors 128, 138 in the perfusate flow direction. The flow sensors 126, 136 may be located downstream of the bubble trap 110. For example, on the portal flow path 120, a flow sensor may be placed upstream of the bubble sensor 134, or alternatively may be placed downstream of the bubble sensor 134. For example, on the hepatic flow path 130, a flow sensor may be placed upstream of the bubble sensor 124, or downstream of the bubble sensor 124. In a method of perfusing the organ 20, the flow sensors 126, 136 may be used to measure a flow rate of the perfusate flowing through a plurality of tubes of the suitable fluid conduit 72 before and/or after, for example, an alteration of the flow balance between the plurality of tubes.

Figure 2:
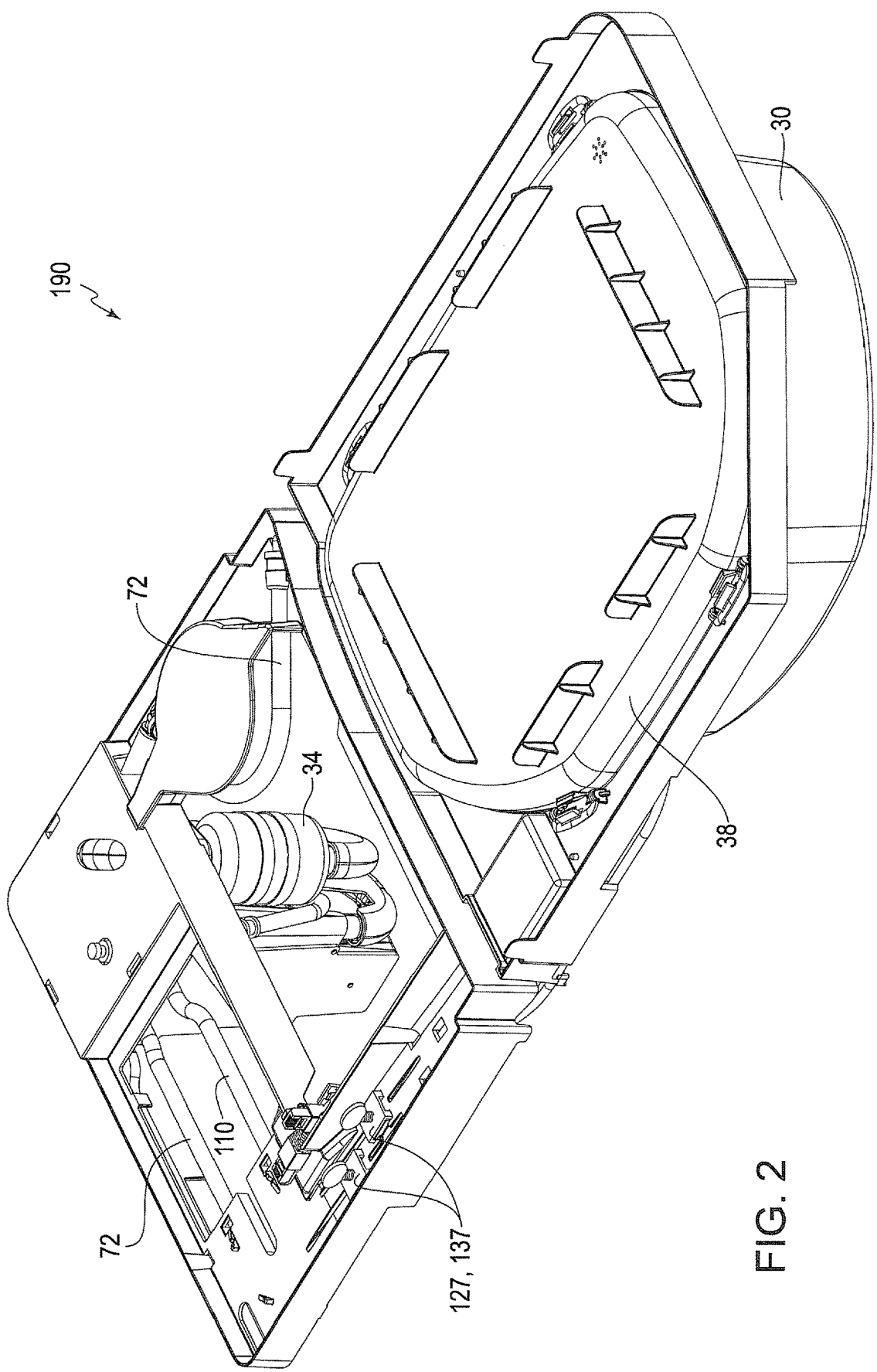
FIG. 2 is a perspective view of an exemplary organ perfusion apparatus including flow control clamps.

Optionally, the controller 400 may provide regulation of the volume, rate and/or pressure of flow that reaches the organ 20, for example, by controlling the pump 80, the bubble trap 110, the valves 122, 132 and/or the flow control clamps 127, 137. For example, the controller 400 may control the pump 80 to apply a fluid motive force to perfusion fluid flowing through the tubes. For example, the controller 400 may control the operation of the bubble trap 110 to vent gas and reduce or eliminate the pulsatility of the perfusate flow. For example, the controller 400 may control the valves 122, 132 to reduce or shut off the fluid flow exiting the bubble trap 110. For example, as discussed above, the controller 400 may control the flow control clamps 127, 137 to fine-tune the flow rate in one or both of the tubes that extend to the organ 20. The controller 400 may also be used to control other aspects of the apparatus 10. Flow control clamps 127, 137 (such as the exemplary clamps shown in FIG. 2) may be used to fine-tune the flow rate in one or both of the tubes that extend to the organ 20, such as the portal flow path 120 and the hepatic flow path 130.

The flow control clamp 127 may be disposed on the fluid conduit 72 between the bubble trap 110 and the organ 20 via the portal flow path 120, and the flow control clamp 137 may be disposed on the fluid conduit 72 between the bubble trap 110 and the organ 20 via the hepatic flow path 130. The flow control clamps 127, 137 may be detachable from the apparatus. The flow control clamps 127, 137 may be disposed anywhere along the tubing of the portal flow path 120 and the hepatic flow path 130. Preferably, the flow control clamps 127, 137 are disposed between the flow sensors 126, 136 and the pressure sensors 128, 138 in the perfusate flow direction.

The flow control clamps 127, 137 may be pinch valves, or any other suitable valves appreciated by one skilled in the art, that function to reduce or shut off flow. As discussed above, pinch valves may be advantageous because they are not in fluid communication with the perfusate. Any flow control device (e.g., a valve such as clamp 127, 137) that is suitable for fine-tuning the flow rate in the tubes may be used by a skilled artisan. The flow control clamps 127, 137 may be either disposable or reusable.

Preferably, the flow control clamps 127, 137 are controllable by a user to alter the flow rate and/or pressure of the perfusate in the portal flow path 120 and/or the hepatic flow path 130. For example, initially, the flow control clamps 127, 137 may be controlled by the user based on a predetermined protocol starting from a condition in which they are completely open or completely closed. For example, the user may engage the flow control clamps 127, 137 to override the flow rate and/or pressure of the perfusate produced by the organ and/or the pump 80. In a method of perfusing the organ 20, the flow control clamps 127, 137 may be used to alter the flow balance between two tubes of the suitable fluid conduit 72 without altering the fluid motive force that is applied, for example, by the pump 80. For example, the flow balance between the two tubes may be altered by selecting and actuating (for example, by manually controlling) at least one of the flow control clamps 127, 137 to constrict at least one of the two tubes. After altering the flow balance, a new flow balance may be established. A period of time may pass before the new flow balance is established, and the controller 400 may measure the period of time.

The apparatus 10 may include optional components in the form of devices, such as mechanical and/or electrical devices, and/or computer programming. For example, the apparatus 10 may include a detector (for example, an optical sensor, a mechanical switch, a Hall effect sensor, or any other suitable components appreciated by one skilled in the art) or embedded firmware to communicate with, for example a computer-readable chip, to detect the presence or absence of the flow control clamps 127, 137, other valve mechanisms and/or other components. For example, the detector may configured to detect an optional component of the apparatus (e.g., the flow control clamps 127, 137 and/or other components, as discussed above), and may provide a signal to the controller indicative of the presence of the optional component. The optional component may be part of a disposable component used with the apparatus. The optional component may be programming for the controller 400. The optional component may be an electronic device, and the electronic device may be part of the disposable component for use with the apparatus.

The computer-readable chip may be programmed with, for example, an identifier (e.g., a serial number) that will indicate to the apparatus 10 that a manual flow control clamp model is to be used. The model may be programmed with unique software that would allow the user to utilize different modes of operation. The model may be programmed with software that allows the user to program a specific flow rate and/or control regime in two tubes independent of each other. The model may be programmed with software that allows the user to set a pressure limit hard stop, or allows the user to set a "pressure preferred" mode that allows flow rate to fluctuate while holding a given set point for pressure. The apparatus 10 may be controlled based on a first mode of operation when the detector does not detect the presence of the flow control clamps 127, 137 on the tubing. The first mode of operation may allow the organ 20 and pump 80 to control the flow rate and/or pressure of the perfusate in the portal flow path 120 and the hepatic flow path 130. The apparatus 10 may be controlled based on a second mode of operation when the detector detects the presence of the flow control clamps 127, 137 on the tubing. The second mode of operation may allow the user to adjust the flow control clamps 127, 137 to override the flow rate and pressure produced by the organ 20 and/or the controller 400. The flow control clamps 127, 137 may be adjusted manually, for example. This configuration may be advantageous because it allows a clinician to override, for example, predetermined flow rates in the portal flow path 120 and the hepatic flow path 130, and instead operate the apparatus 10 under different conditions. This allows clinician to have additional flexibility to change specific parameters of the apparatus 10, e.g., the flow rate of the perfusate through the organ. For example, this may be advantageous for clinicians who may want to explore flow rates and/or pressures that are not based on a pre-programmed algorithm provided with the apparatus 10 to establish a flow rate and/or pressure, and instead may want to evaluate alternative control and/or perfusion schemes to determine clinical outcomes. The second mode of operation may change how components of the apparatus 10 operate. For example, alarms may be disabled, or modes of operation may be changed, such as how fast the pump 80 operates and/or how frequently sensors sample data.

When the detector detects the presence of one or both of the flow control clamps 127, 137 on the tubing, the apparatus 10 may preferably be controlled based on the second mode of operation that allows the user to adjust one or more of the flow control clamps 127, 137 to override the flow rate produced by the pump 80, organ 20 and/or the controller 400. The pressure sensors 128, 138 may be configured to detect the flow rate of the perfusate continuously, periodically, or after the user adjusts one or more of the flow control clamps 127, 137. In addition, or alternatively, the flow sensors 126, 136 may be configured to detect the flow rate of the perfusate continuously, periodically, or after the user adjusts one or more of the flow control clamps 127, 137. Detection of the flow rate immediately after adjustment of one or more of the flow control clamps 127, 137 may be advantageous because the output of the pressure sensors 128, 138 may be inaccurate or delayed immediately following user adjustment of the flow control clamps 127, 137. Thus, when the flow control clamps 127, 137 are engaged, the apparatus 10 can rely on the flow sensors 126, 136 as back-up sensors to more accurately determine the flow rate and/or pressure of the perfusate.

As discussed above, in self-regulated flow in which the organ 20 and pump 80 control the amount of flow that is divided between the portal flow path 120 and the hepatic flow path 130, pressure sensors 128, 138 provide overpressure monitoring. In the event that pressure delivered to the organ in either or both of the portal flow path 120 and the hepatic flow path 130 exceeds a predetermined threshold, the apparatus 10 can automatically stop and/or reduce the flow rate and/or pressure provided by the pump 80 to prevent damage to the organ. For example, if the controller 400 determines that the pressure in the portal flow path 120 and/or the hepatic flow path 130 exceeds a predetermined range, the controller 400 may control the pump 80 to slow down or stop operation and provide a warning signal to the user. If the controller 400 determines that the pressure in one tube (e.g., of the portal flow path 120 or the hepatic flow path 130), and not both tubes, exceeds the predetermined range, the controller 400 may optionally adjust the flow control clamp 127, 137 disposed on the tube to alleviate overpressure. In addition or alternatively, the pressure sensors 128, 138 may be used to generate warning signals to the user and/or to the controller 400 as pressures approach the predetermined threshold.

After exiting one or both of the portal flow path 120 and hepatic flow path 130, perfusate flows through the organ and returns to the basin 30 to form an organ bath. For example, the perfusate may free flow out of the organ and collect in the basin 30.

Bypass flow path 140 may include a valve 142, and/or sensors such as oxygen sensor 144 and pH sensor 146. Preferably, the valve 142 is a pinch valve and may be of similar configuration to valves 122 and 132, but any suitable valve may be used. The oxygen sensor 144 and the pH sensor 146 may be used to determine the state of the perfusate. Preferably, the bypass flow path 140 is only used during a purging or priming process, although it may also be used during perfusion, optionally continuously, to monitor perfusate properties in real time.

The organ perfusion apparatus 10 may also include an accelerometer 150. Preferably the accelerometer 150 is a three-axis accelerometer, although multiple single axis accelerometers may be used to the same effect. The accelerometer 150 may be used to continuously or periodically monitor and/or record the state of the apparatus 10. Monitoring may include monitoring for excessive shocks as well as attitude of the apparatus 10. By implementing such monitoring, misuse or potentially inappropriate conditions of the apparatus 10 can be detected and recorded.

The apparatus 10 may include storage compartments for items other than the organ 20. For example, the apparatus 10 may include a document compartment 160 to store documents and/or charts related to the organ 20. Also, the apparatus 10 may include one or more sample compartment. The sample compartment 10 may be configured, for example, to store fluid and/or tissue samples. The sample compartment may be advantageously disposed near the coolant container 50 to provide cooling, which may be similar or equivalent to the cooling provided for the organ 20.

The apparatus 10 may include one or more tamper evident closures 80. A tamper evident closure may be used to alert a user that the apparatus 10 has been opened at an unauthorized time and/or location and/or by an unauthorized person. Evidence of tampering may alert the user to perform additional testing, screening, or the like before using the organ 20 and/or the apparatus 10.

Preferably, all components of the apparatus 10 that come into contact with perfusate and/or the organ 20 are disposable and/or easily replaced. Such disposable items may be included in a kit or saleable package. This allows the sterilized, disposable components to be "single-use" components. That is, once an organ 20 is placed in the basin 70, such sterilized, disposable components may be discarded without being used for another organ. For example, such a kit may include packaging such as plastic or shrink wrap packaging containing some or all of the components that come into contact with an organ 20 and/or perfusate. In exemplary implementations, the tubing, filter, oxygenator and bubble trap are packaged together in a manner preconfigured to be placed into a flow path arrangement of fixed-location parts in apparatus 10, and the cradle and basin are packaged individually or together, and optionally together with the tubing, filter, oxygenator and bubble trap. Accordingly, the organ perfusion apparatus 10 maintains strict sterility and prevents contamination of an organ 20 being perfused in the apparatus 10. The components of the apparatus 10 that are not disposable may be selected such that they can be reused indefinitely. If the flow sensors 126, 136 and flow control clamps 127, 137 (or any other flow control devices, e.g., valves) are designed to come into contact with the perfusate, they are preferably disposable and may be packaged in the kit.

What has been described and illustrated herein are preferred exemplary implementations of the invention along with some variations. The terms, descriptions and figures used herein are set forth by way of illustration only and are not meant as limitations. Those skilled in the art will recognize that many variations are possible within the spirit and scope of the invention.

What is claimed is:

1. A method of perfusing an organ or tissue, the method comprising:
    connecting a conduit to an organ or tissue, the conduit comprising a plurality of tubes, and a first end of each of at least two said tubes being connected to the organ or tissue;
    applying a fluid motive force to a perfusion fluid in the at least two tubes to force the fluid through the at least two tubes into the organ or tissue to perfuse the organ or tissue;
    allowing a flow balance to be established between the at least two tubes by the fluid motive force and backpressure generated by the organ or tissue being perfused;
    after the flow balance has been established by the fluid motive force and the backpressure, then altering the flow balance between the at least two tubes without altering the fluid motive force that is applied; and
    sensing, by a sensor, the presence or absence of at least one device configured to alter the flow balance between the at least two tubes without altering the fluid motive force that is applied.

2. A method of perfusing an organ or tissue, the method comprising:
    connecting a conduit to an organ or tissue, the conduit comprising a plurality of tubes, and a first end of each of at least two said tubes being connected to the organ or tissue;
    applying a fluid motive force to a perfusion fluid in the at least two tubes to force the fluid through the at least two tubes into the organ or tissue to perfuse the organ or tissue;
    allowing a flow balance to be established between the at least two tubes by the fluid motive force and backpressure generated by the organ or tissue being perfused; and
    sensing, by a sensor, the presence or absence of at least one device configured to alter the flow balance between the at least two tubes without altering the fluid motive force that is applied.

3. The method according to claim 2, further comprising controlling the flow of the perfusion fluid differently if the at least one device is detected than if the at least one device is not detected.

4. The method according to claim 3, further comprising if the at least one device is detected, after allowing the flow balance to be established, altering the flow balance between the at least two tubes without altering the fluid motive force that is applied.

5. The method according to claim 2, wherein the sensor is at least one of an optical detector, a mechanical switch, and a Hall effect sensor.

6. The method according to claim 2, wherein:
    the at least one device is configured to be attached to and detached from the at least two tubes; and
    the sensor is configured to sense the presence or absence of the at least one device on at least one of the at least two tubes.

* * * * *